United States Patent [19]
Shemesh et al.

[11] Patent Number: 5,928,166
[45] Date of Patent: Jul. 27, 1999

[54] BLOOD SAMPLING APPARATUS

[75] Inventors: Eli Shemesh, Ashdod; Zvi Levinhar, Neve Monoson; Eitan Rogel, Haifa, all of Israel

[73] Assignee: Migada, Inc., N.J.

[21] Appl. No.: 08/860,410

[22] PCT Filed: Jan. 11, 1996

[86] PCT No.: PCT/US96/00321

§ 371 Date: Apr. 16, 1998

§ 102(e) Date: Apr. 16, 1998

[87] PCT Pub. No.: WO96/21393

PCT Pub. Date: Jul. 18, 1996

[30] Foreign Application Priority Data

Jan. 13, 1995 [IL] Israel ......................................... 112339
May 2, 1995 [IL] Israel ......................................... 113590

[51] Int. Cl.⁶ .................................................... A61B 5/00
[52] U.S. Cl. ............................................................ 600/576
[58] Field of Search .................................. 600/576–578, 600/583; 604/411–414, 283

[56] References Cited

U.S. PATENT DOCUMENTS

| | | | |
|---|---|---|---|
| 2,955,595 | 10/1960 | Semple | 600/577 |
| 3,841,835 | 10/1974 | Kishimoto et al. | 23/253 |
| 3,872,730 | 3/1975 | Ringrose et al. | 73/421 |
| 3,877,465 | 4/1975 | Miyake | 128/2 F |
| 4,266,543 | 5/1981 | Blum | 128/218 |
| 4,763,648 | 8/1988 | Wyatt | 128/673 |
| 4,774,964 | 10/1988 | Bonaldo | 128/763 |
| 4,790,827 | 12/1988 | Haber et al. | 604/198 |
| 4,843,017 | 6/1989 | Oberhardt et al. | 436/177 |
| 4,920,970 | 5/1990 | Wyatt | 128/673 |
| 4,934,015 | 6/1990 | Mink | 15/268 |
| 4,981,140 | 1/1991 | Wyatt | 128/673 |
| 5,002,066 | 3/1991 | Simpson et al. | 128/760 |
| 5,303,713 | 4/1994 | Kurose | 128/763 |
| 5,360,012 | 11/1994 | Ebara et al. | 128/764 |
| 5,552,118 | 9/1996 | Mayer | 600/577 |

*Primary Examiner*—Max Hindenburg
*Attorney, Agent, or Firm*—Ladas & Parry

[57] ABSTRACT

Blood sampling apparatus operative to selectively and removably interconnect a blood sample container with an extracorporeal blood conduit and including a blood interface assembly adapted to securely and removably puncture both said blood conduit and said blood sample container, the blood interface assembly comprising an elongate housing, a needle mount removably mounted in said elongate housing, a double pointed needle fixedly adhesively mounted in said needle mount so as to have portions extending outward of said needle mount in opposite directions and a puncturable resilient sheath formed over at least one portion of said needle and onto at least a portion of said needle mount.

7 Claims, 12 Drawing Sheets

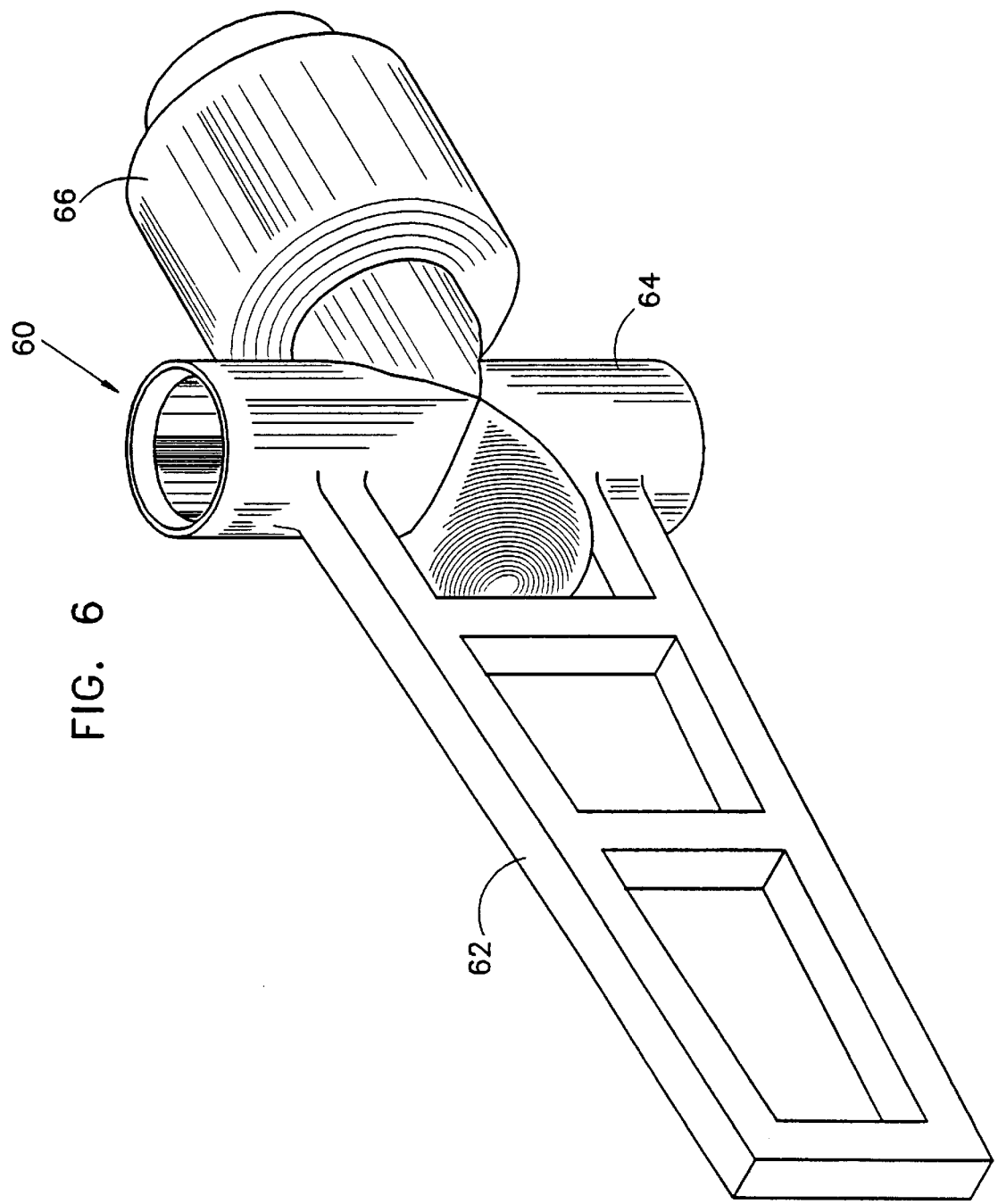

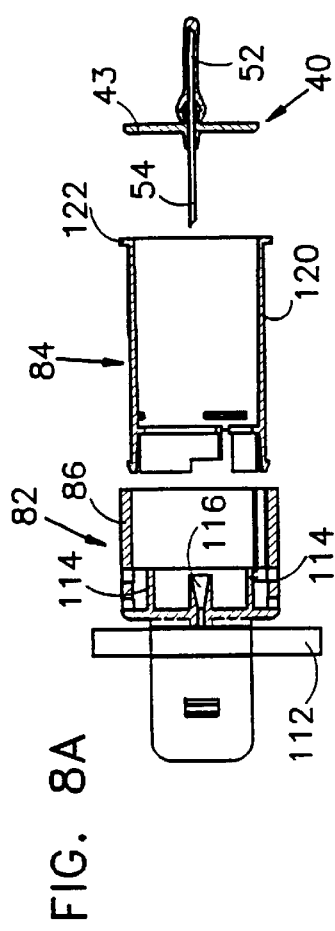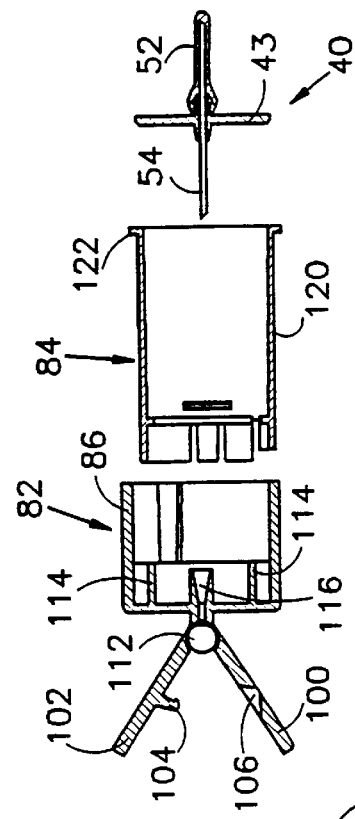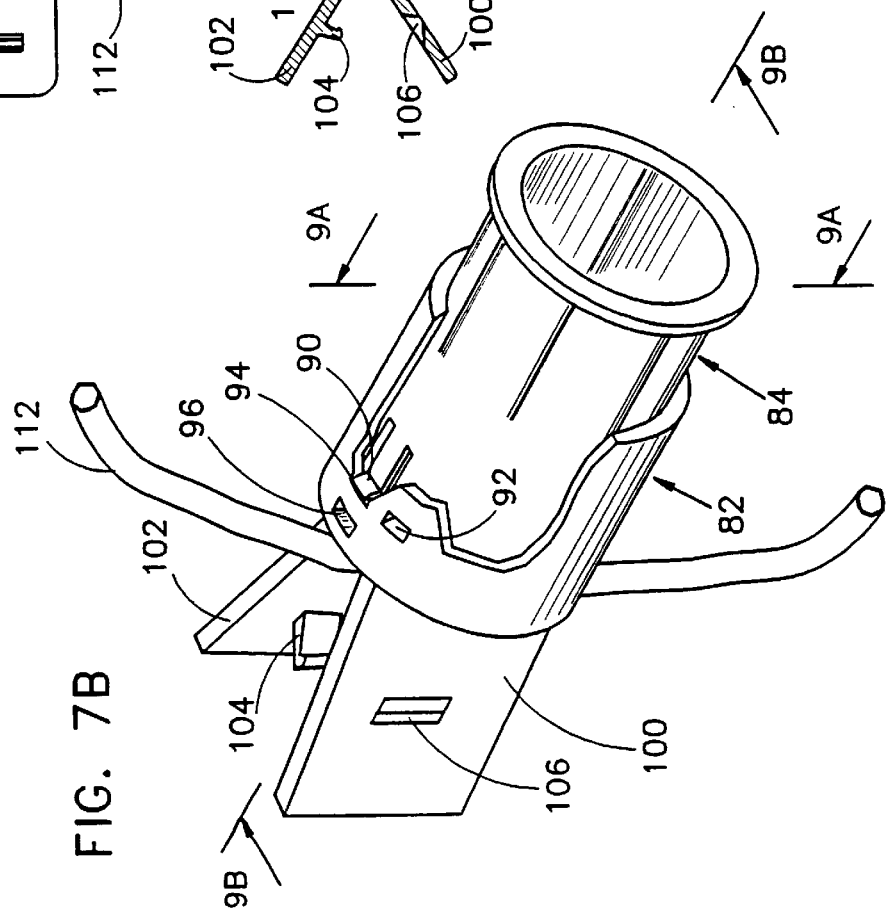

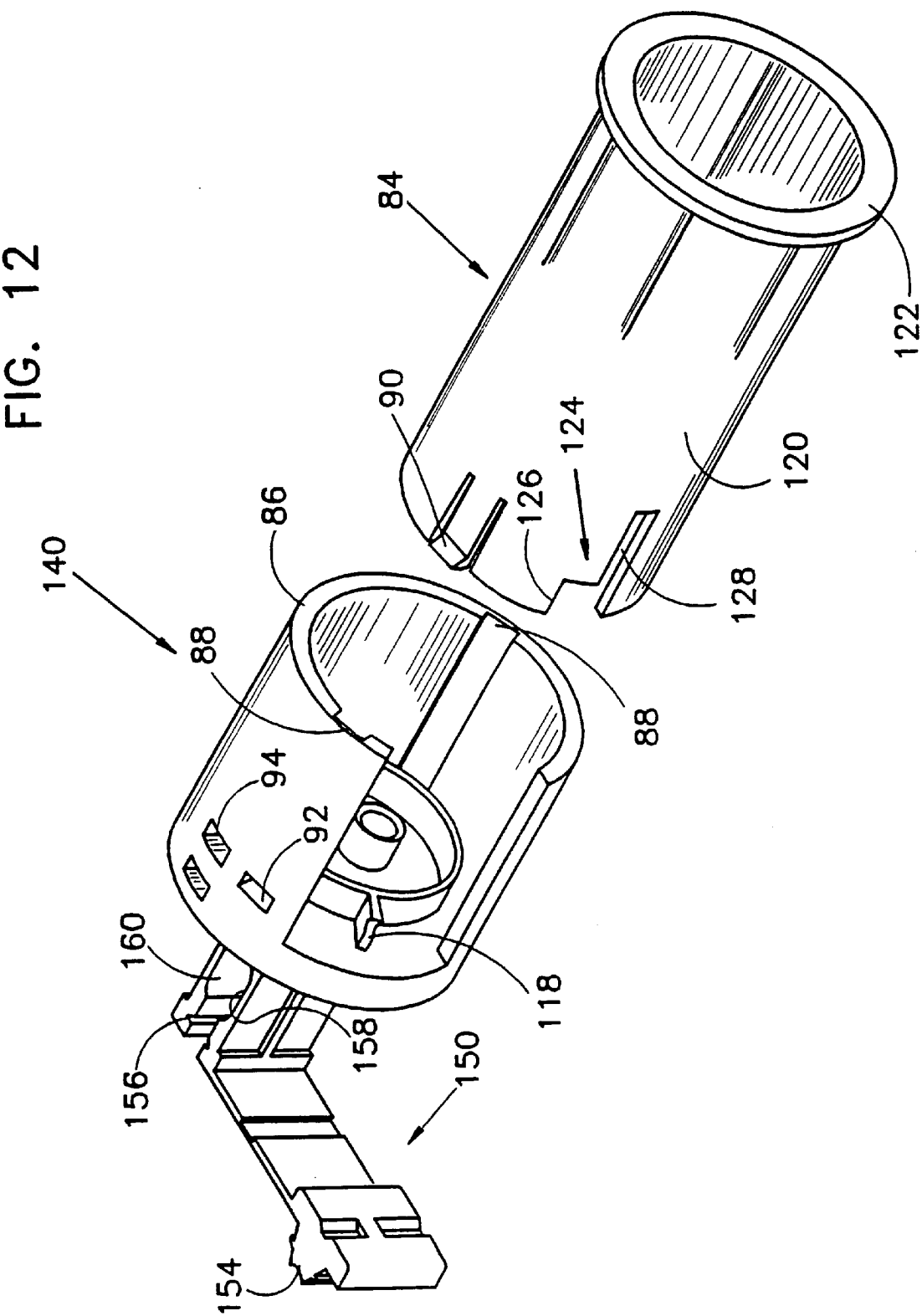

BLOOD SAMPLING APPARATUS

This application is a 371 of PCT/US 96/00321 filed Jan. 11, 1986.

FIELD OF THE INVENTION

The present invention relates to blood sampling apparatus generally.

BACKGROUND OF THE INVENTION

Various types of blood sampling apparatus are known in the art. The following patent documents are believed to represent the state of the art: U.S. Pat. Nos. 3,877,465; 4,763,648; 4,920,970; 4,934,015; 4,981,140; 5,002,066 & 5,084,034; European Patent Application 88906129.7 and PCT Published Patent Application WO 93/21821.

SUMMARY OF THE INVENTION

The present invention seeks to provide improved blood sampling apparatus having enhanced safety features.

There is thus provided in accordance with a preferred embodiment of the present invention blood sampling apparatus operative to selectively and removably interconnect a blood sample container with an extracorporeal blood conduit and including:

a blood interface assembly adapted to securely and removably puncture both said blood conduit and said blood sample container, the blood interface assembly comprising:
an elongate housing;
a needle mount removably mounted in said elongate housing;
a double pointed needle fixedly adhesively mounted in said needle mount so as to have portions extending outward of said needle mount in opposite directions; and
a puncturable resilient sheath formed over at least one portion of said needle and onto at least a portion of said needle mount. In accordance with a preferred embodiment of the invention, the housing is configured and the needle is mounted such that inadvertent engagement of a user's finger with either point of said needle is substantially prevented.

Additionally in accordance with a preferred embodiment of the present invention, the removable mounting of the needle mount into said housing is effected by a plurality of tabs, azimuthally distributed about the interior periphery of the housing spaced from a peripheral shoulder formed therein.

Further in accordance with a preferred embodiment of the present invention, the adhesive mounting of the double-pointed needle in the needle mount is provided by application of adhesive on only one side of the needle mount and onto a roughened portion of the needle.

Preferably, the adhesive is configured so as to provide an inclined surface over which an open end of the resilient sheath is readily slid into retained engagement with an axially extending portion of said needle mount.

In accordance with a preferred embodiment of the present invention, the needle mount comprises a truncated circular disk having integrally formed therewith a pair of male needle attachment portions.

Further in accordance with another preferred embodiment of the present invention, there is provided blood sampling apparatus which further includes a puncturable sampling appliance adapted to be mounted onto the blood conduit such that the blood conduit extends uninterrupted therethrough and can be punctured thereat to draw blood therefrom.

Additionally in accordance with a preferred embodiment of the present invention, the puncturable sampling appliance is configured and the needle is mounted such that inadvertent engagement of a user's finger with a point of the needle extending towards the puncturable sampling appliance is substantially prevented.

Still further in accordance with a preferred embodiment of the present invention, the blood interface assembly is adapted to engage with the puncturable sampling appliance in first and second engagements, wherein in the first engagement, the needle is prevented from puncturing the blood conduit, and wherein in the second engagement, the needle is allowed to puncture the blood conduit.

Additionally in accordance with a preferred embodiment of the present invention, the blood interface assembly is adapted to engage with the puncturable sampling appliance in first and second engagements,
wherein in the first engagement, the blood interface assembly is substantially prevented from axial movement with respect to the puncturable sampling appliance and the needle is prevented from puncturing the blood conduit, the blood interface assembly being rotatable azimuthally with respect to the puncturable sampling appliance, and
wherein in the second engagement, the blood interface assembly may be moved axially with respect to the puncturable sampling appliance, thereby causing the needle to puncture the blood conduit.

BRIEF DESCRIPTION OF DRAWINGS

The present invention will be understood and appreciated more fully from the following detailed description, taken in conjunction with the drawings in which:

FIG. 6 is a pictorial illustration of a puncturable sampling appliance constructed and operative in accordance with another preferred embodiment of the present invention;

FIGS. 7A and 7B are respective exploded view and partially assembled pictorial illustrations of another preferred embodiment of blood sampling apparatus useful without pre-fitted blood conduit puncture defining elements;

FIGS. 8A and 8B are sectional exploded illustrations of the blood sampling apparatus of FIGS. 7A and 7B corresponding to FIGS. 9A and 9B;

FIG. 12 is a partially assembled pictorial illustration of yet another preferred embodiment of blood sampling apparatus useful without pre-fitted blood conduit puncture defining elements;

DETAILED DESCRIPTION OF PREFERRED EMBODIMENTS

Figure 1:
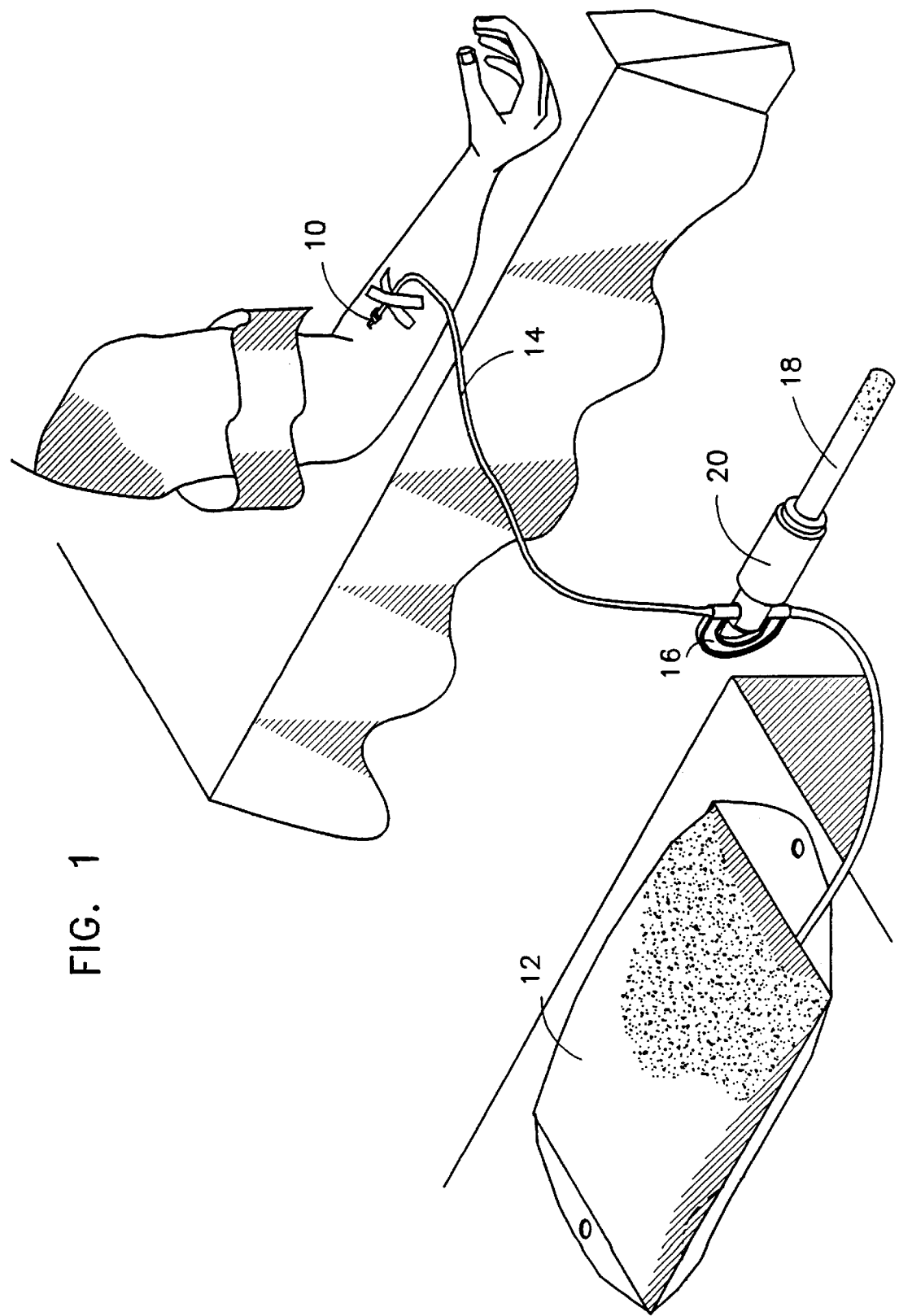
FIG. 1 is a simplified pictorial illustration of a blood sampling system constructed and operative in accordance with a preferred embodiment of the present invention.
Figure 2:
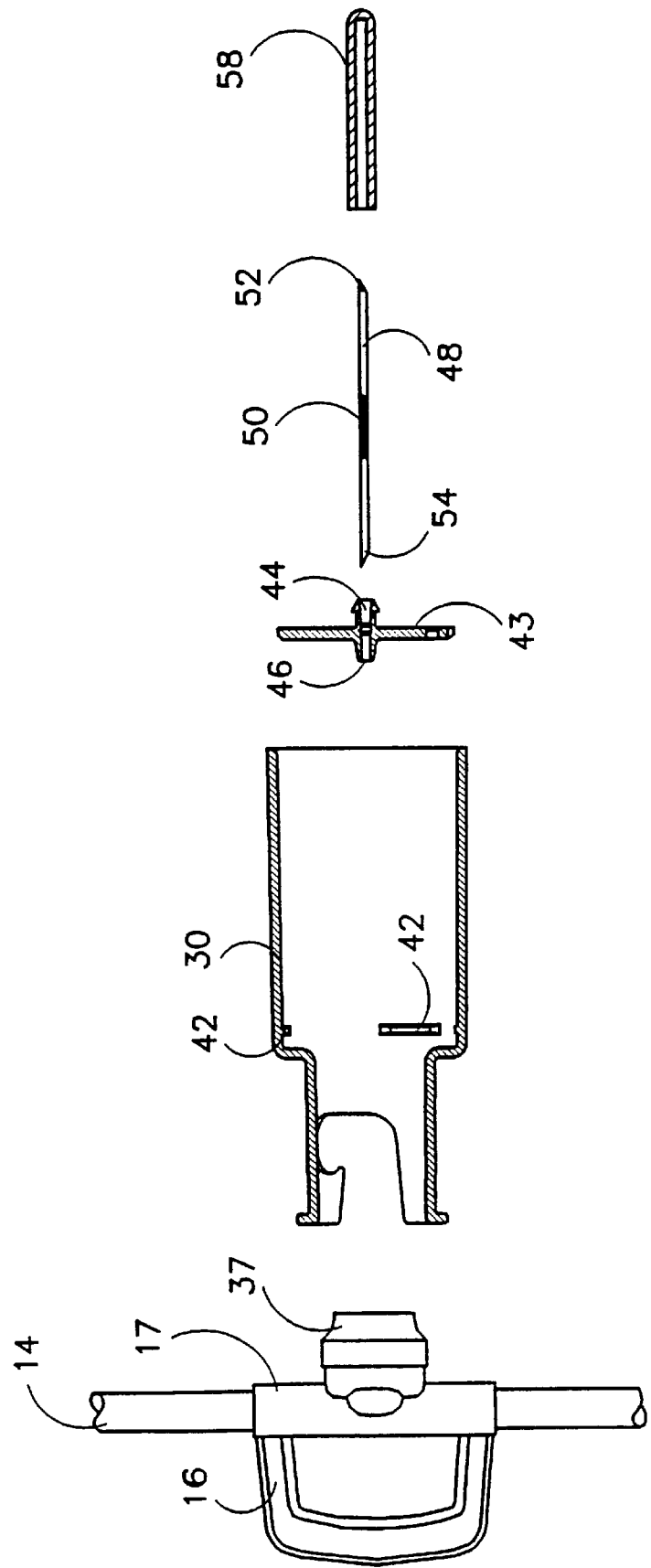
FIG. 2 is an exploded view illustration of an interface assembly useful in the system of FIG. 1.

Reference is now made to FIGS. 1 and 2, which illustrates a blood sampling system constructed and operative in accordance with a preferred embodiment of the present invention. The blood sampling system comprises a needle assembly 10, which is inserted into the vein of a person from whom blood is drawn, a blood collection container 12 and a conduit 14 interconnecting the needle assembly 10 to the blood collection container 12, such that blood is drawn via needle assembly 10 via conduit 14 to container 12.

A puncturable sampling appliance 16 is preferably mounted onto conduit 14. As seen in FIG. 2, appliance 16 preferably has a hollow portion 17 such that conduit 14 extends uninterrupted therethrough and can be punctured thereat to draw blood from conduit 14. Preferably the appliance 16 also has an interface assembly receiving portion 37.

A blood sampling tube 18 is removably attached to a blood sampling interface assembly 20, which in turn is removably attached to appliance 16 for drawing blood from conduit 14 into sampling tube 18.

It is a particular feature of the invention that the interface assembly 20 is constructed so as to minimize the possibility of inadvertent engagement of a user's finger with either point of a double pointed needle forming part thereof.

Figure 3:
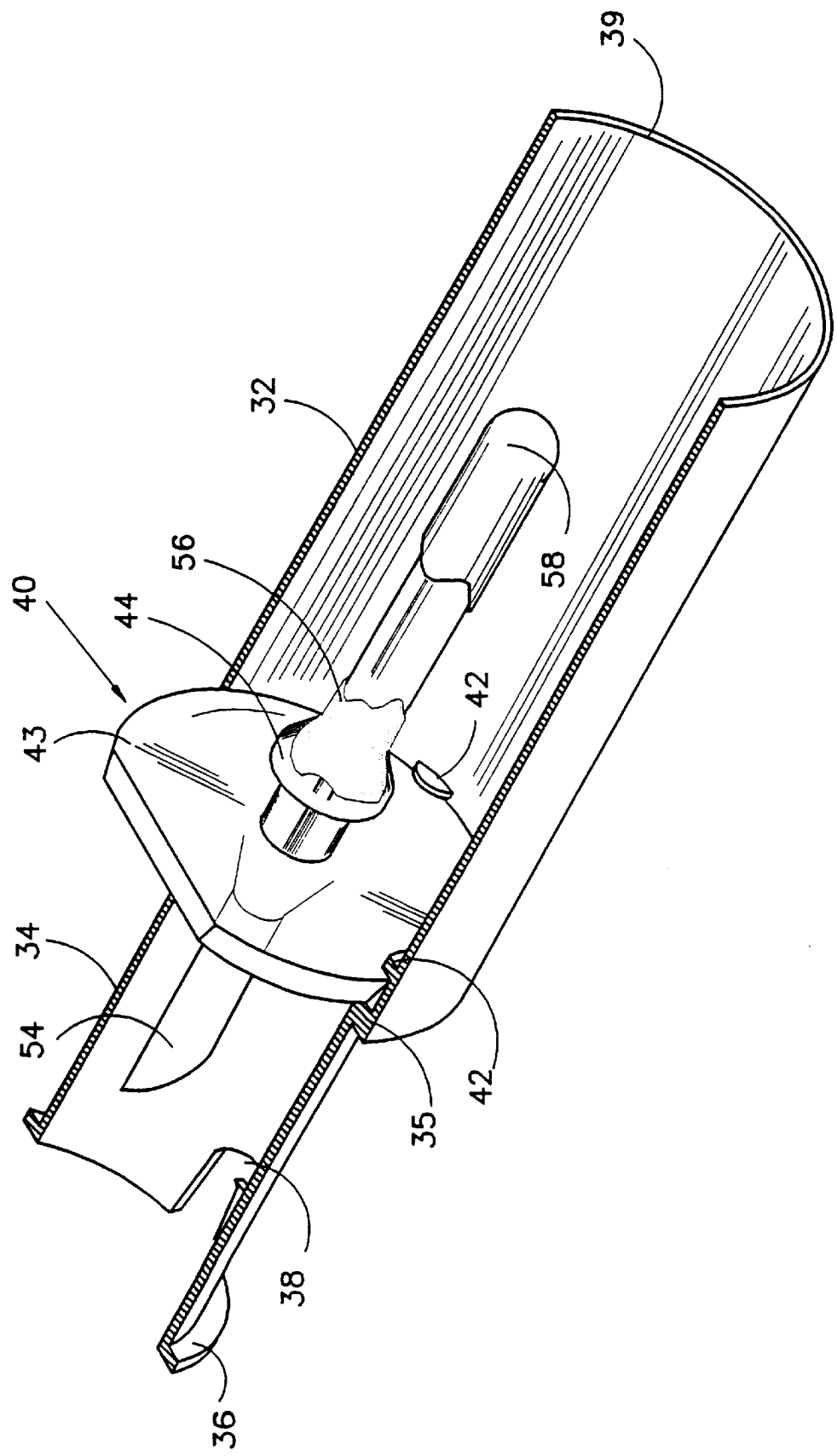
FIG. 3 is a sectional illustration of the interface assembly of FIG. 2.

Reference is now made to FIGS. 2 and 3, which illustrate the construction of the interface assembly 20 of the present invention. As seen in FIGS. 2 and 3, the blood interface assembly comprises an elongate housing 30, typically formed of plastic by injection molding. Housing 30 preferably comprises two generally circular cylindrical portions 32 and 34 which are joined at a shoulder 35. Portion 32 is longer and of larger radius than is portion 34, portion 32 being intended for operative engagement with blood sampling tube 18, while portion 34 is intended for operative engagement with the interface assembly receiving portion 37 of the sampling appliance 16. Preferably, the length of portion 32 is 35 to 50 mm and its inner radius is 9 mm, while the length of portion 34 is 22 mm and its inner radius is 5 mm.

Portion 34 terminates in an outwardly extending flange 36, which communicates with a bayonet-type socket 38. Portion 32 terminates in a circular edge 39.

In accordance with a preferred embodiment of the invention there is provided a separately formed needle mount element 40, which is removably mounted in the elongate housing 30. Element 40 is seated against shoulder 35 and is retained thereagainst by a plurality of inwardly protruding retaining tabs 42.

Needle mount element 40 is preferably formed of plastic by injection molding and includes a planar portion 43 of a truncated conical configuration, integrally formed with a pair of non-identical, hollow, male attachment portions 44 and 46, extending perpendicularly to planar portion 43 at the center of planar portion 43, which is apertured thereat. Preferably, male attachment portion 44 is undercut as clearly shown in FIGS. 2 and 3.

Accordingly, planar portion 43 together with attachment portions 44 and 46 define an elongate channel through which extends a double pointed needle 48, having a roughened center section 50 and a pair of pointed ends 52 and 54.

The double pointed needle 48 is fixedly frictionally and adhesively mounted in the needle mount element 40 so as to have needle portions of differing lengths extending perpendicularly to planar portion 43 outward of the needle mount in opposite directions. Preferably, the point 54 of the needle 48 is spaced at a distance from the shoulder 35 such that when the needle mount element 40 is seated against the shoulder 35 and the assembly 20 is in pierced engagement with the appliance 16, the needlepoint 54 pierces the conduit 14 and is positioned substantially along the central axis of the conduit 14, as seen clearly in FIG. 4. Preferably, point 52 of needle 48 is located at a distance of 20 to 35 mm interiorly of the end edge 39 of portion 32, while point 54 of needle 48 is located at a distance of 10 to 15 mm interiorly of flange 36.

An adhesive 56, such as U. V. adhesive, is preferably disposed about an outward edge of attachment portion 44 in such a manner so as to provide a smooth transition between the outer surface of the needle and the maximum diametral dimension of the attachment member. This particular arrangement enables relatively easy sliding of the open end of a puncturable resilient sheath 58 thereover into frictionally retained engagement with the attachment member 44, as seen particularly well in FIG. 4. It is seen in FIG. 4 that preferably, the open end of the sheath 58 engages the undercut formed in attachment portion 44, for enhanced retention thereon.

Figure 4:
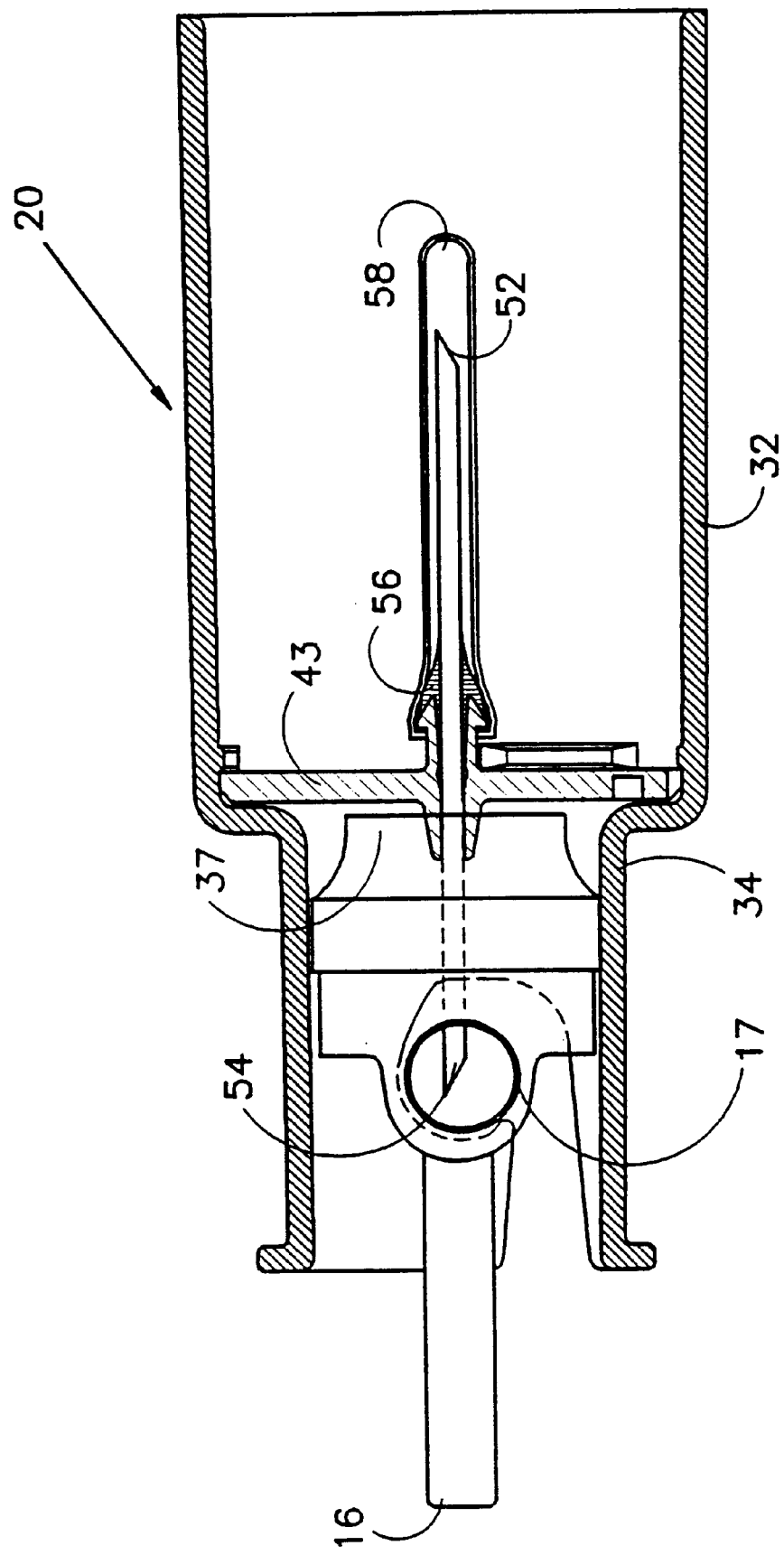
FIG. 4 is a sectional illustration of puncturing engagement of the interface assembly with a blood conduit in accordance with a preferred embodiment of the present invention.

FIG. 4 illustrates operative engagement between interface assembly 20 and appliance 16 and more specifically puncturing engagement of needle point 54 with the interior of conduit 14 via appliance 16. It is seen that bayonet type socket 38 engages the outer perimeter of the hollow portion 17 for retaining the interface assembly 20 onto appliance 16.

Figure 5:
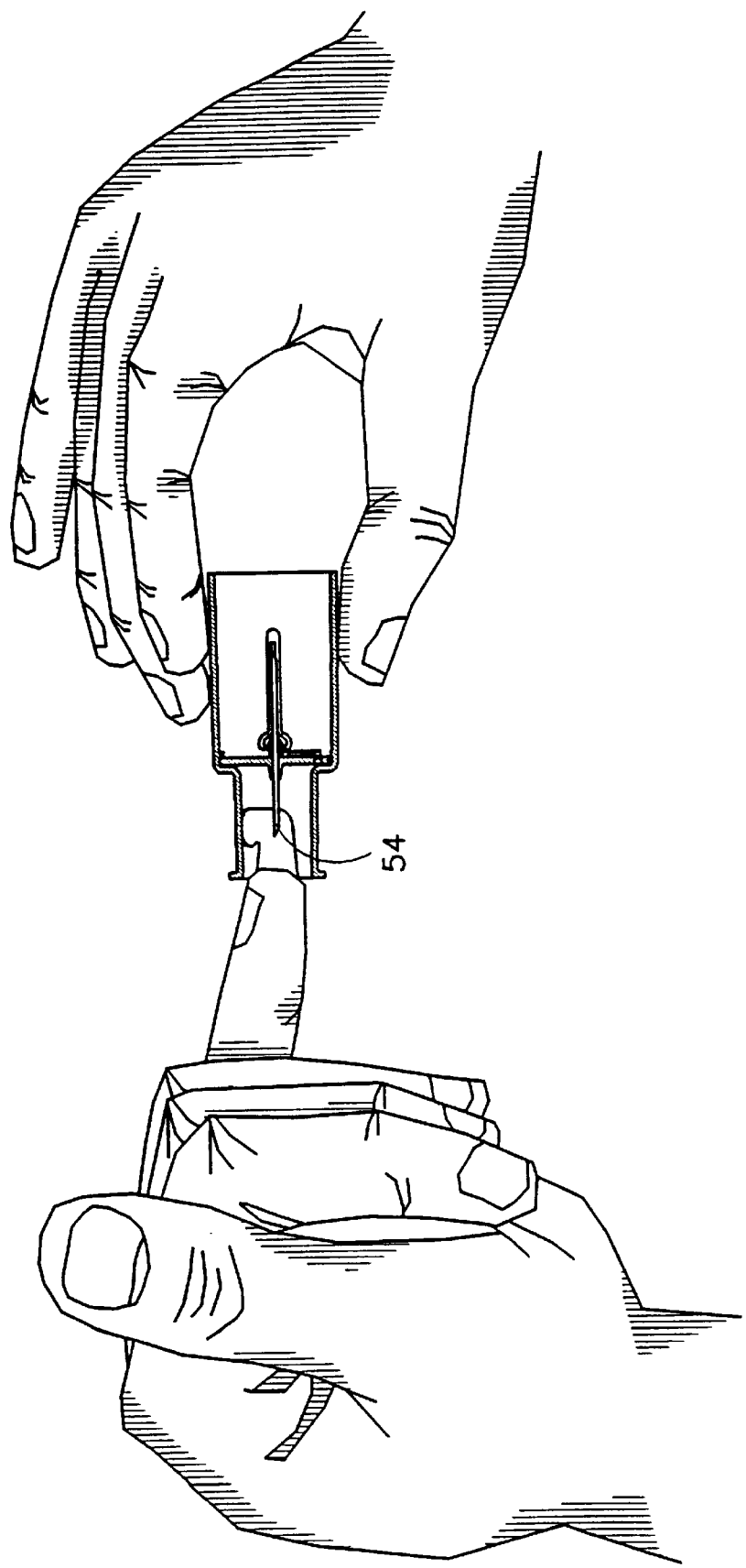
FIG. 5 is a pictorial illustration showing how the interface assembly is resistant to inadvertent engagement between a user's fingers and a needle point.

FIG. 5 illustrates how inadvertent engagement of a user's finger with needle point 54 is minimized by the structure of the present invention.

Reference is now made to FIG. 6, which is a pictorial illustration of a puncturable sampling appliance 60 constructed and operative in accordance with an alternative embodiment of the present invention. The appliance 60 comprises an elongate handle portion which is integrally formed, as by injection molding, with a channel defining portion 64 through which passes a blood conduit (not shown).

Communicating with the interior of channel defining portion 64 is an interface assembly receiving portion 66 which is substantially identical in configuration and operation to the interface assembly receiving portion 37 of the sampling appliance 16 shown in FIG. 2.

Reference is now made to FIGS. 7A–11B, which illustrate blood sampling apparatus 80 constructed and operative in accordance with another preferred embodiment of the present invention. Whereas the apparatus shown in FIGS. 1–6 is intended for use in an environment wherein a puncturable sampling appliance is prefitted onto a blood conduit, the apparatus of FIGS. 7–11B is intended for use in environments where no puncturable sampling appliance is present on the blood conduit.

Referring particularly to FIGS. 7A–9B it is seen that the blood sampling apparatus 80 comprises a snap-engageable puncturable blood conduit engaging element 82 and a snap fittable interface element 84. Element 82 is preferably integrally formed, as by injection molding, of a single piece of plastic and includes a generally circular cylindrical portion 86 having a pair of elongate axially directed slots 88 formed on opposite sides of the interior surface thereof, for accommodating corresponding resilient protrusions 90 formed on the interface element 84.

Associated with each of elongate slots 88 are a plurality of apertures indicated by reference numerals 92, 94 and 96, whose functionality will be described in detail hereinbelow. An aperture 92 is aligned with each slot 88, while an aperture 94 is disposed azimuthally alongside each aperture 92. An additional aperture 96 is disposed in axial alignment with each aperture 94 at a location intermediate aperture 94 and an end surface 98 of the cylindrical portion 86.

Figure 10:
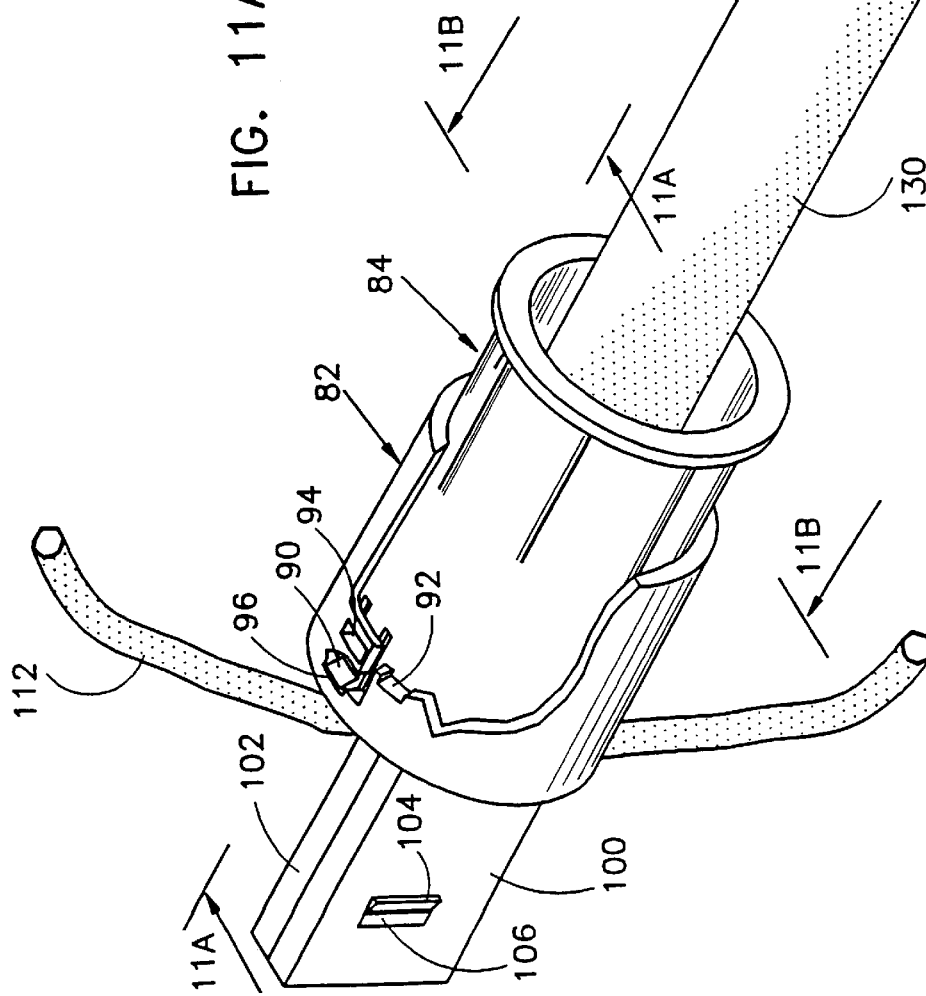
FIG. 10 is a pictorial illustration of the apparatus of FIGS. 7–9B in operative engagement with a blood sampling tube.

Associated with portion 86 are a pair of cooperating butterfly clamp portions 100 and 102, one of which is formed with a resilient hook 104 and the other with a corresponding socket 106. Clamp portions 100 and 102 are formed with corresponding mutually facing transverse recesses 108 and 110 which are configured and arranged to accommodate a blood conduit 112 (FIG. 7B), when the clamp portions 100 and 102 are held together by the engagement of hook 104 in socket 106, as seen in FIG. 10.

Figure 7A:
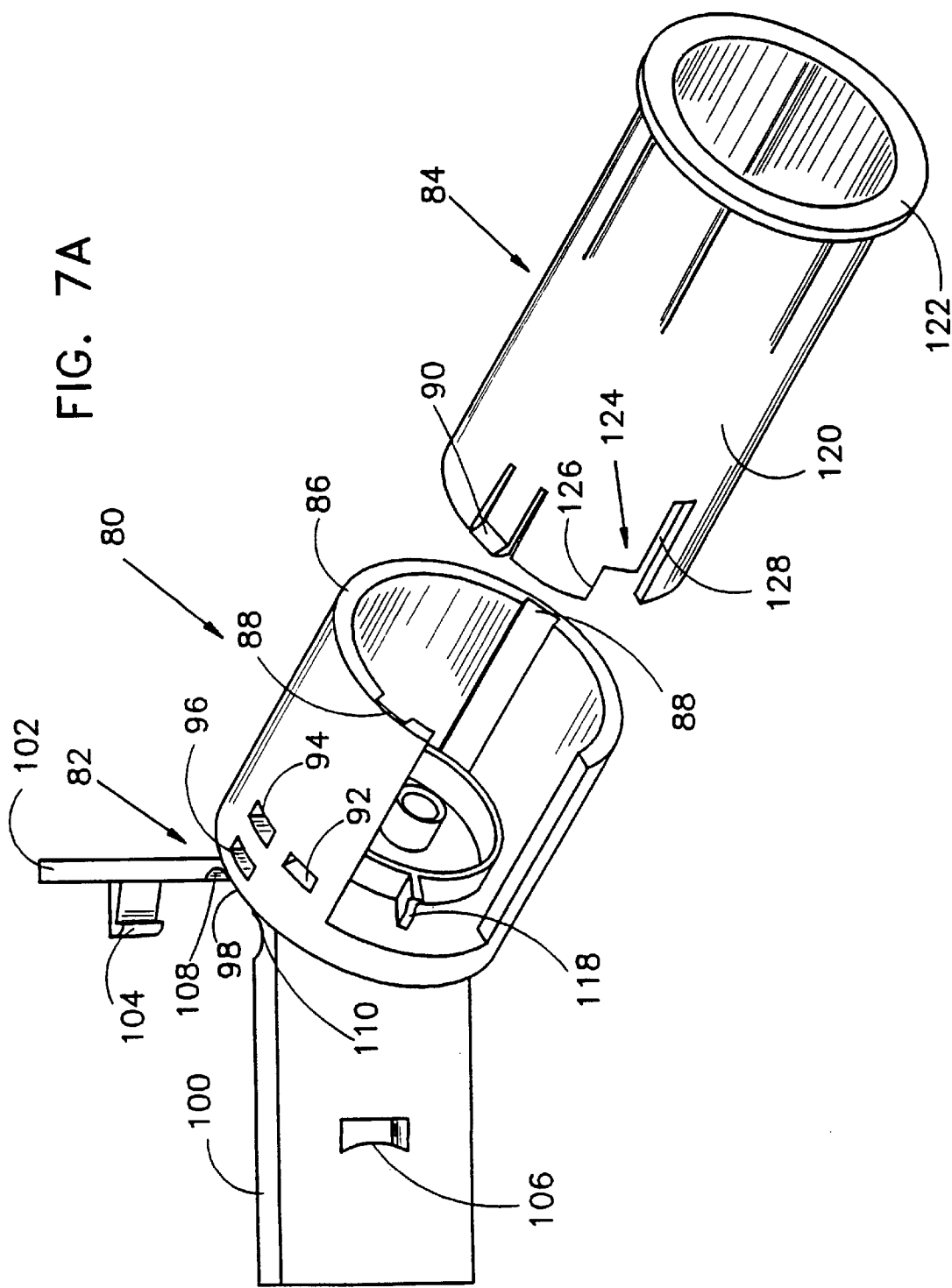

As seen particularly in FIGS. 8A and 8B, portion 86 defines an interior circular protrusion 114 and coaxially therewith a central needle passage 116 which communicates with sockets 108 and 110 so as to enable a needle passing through passage 116 to engage and puncture a blood conduit 112. Interior circular protrusion 114 is connected with the cylindrical wall of portion 86 by a pair of mutually 180 degree spaced ribs 118, as seen in FIG. 7A.

The interface element 84 comprises a generally circular cylindrical tube like portion 120 having at one end thereof an outwardly directed flange 122. At an end of portion 120, opposite to the end at which flange 122 is located, there are provided a pair of mutually 180 degree spaced two step notches 124. Notches 124 are preferably located azimuthally offset by 90 degrees from the protrusions 90. Each notch 124 comprises a relatively wide, axially relatively shallow step 126 and a relatively narrow, axially relatively deep step 128. The pair of ribs 118 of engaging element 82 are arranged such that when each protrusion 90 is aligned with a corresponding aperture 92, each rib 118 is aligned with each shallow step 126. When each protrusion 90 is aligned with corresponding apertures 94 and 96, each rib 118 is aligned with a corresponding deep step 128.

The operation of sampling appliance 80 will now be described in detail. The sampling appliance 80 is supplied to a user with the needle mount element 40 assembled with the interface element 84 and the interface element 84 in engagement with the engaging element 82, wherein the protrusions 90 are engaged with the corresponding apertures 92, which lie along slots 88. The foregoing configuration is hereafter termed a first engagement. The protrusions 90 and the apertures 92 are constructed such that the user can not pull the interface element 84 axially out of engagement with engaging element 82, but rather the protrusions 90 can only slide azimuthally from apertures 92 to apertures 94.

In the first engagement each relatively shallow step 126 butts against the corresponding rib 118, thereby preventing the needle point 54 from puncturing the blood conduit 112. It is appreciated that in the first engagement, a user's finger is substantially shielded by the engaging element 82 from needle point 54 and from inadvertent puncture therewith.

Figure 9A:
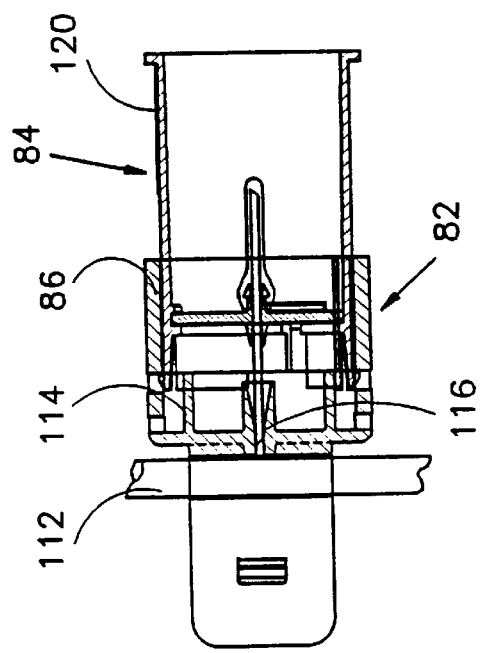
FIGS. 9A and 9B are sectional illustrations taken along respective lines 9A—9A and 9B—9B in FIG. 7B.
Figure 9B:
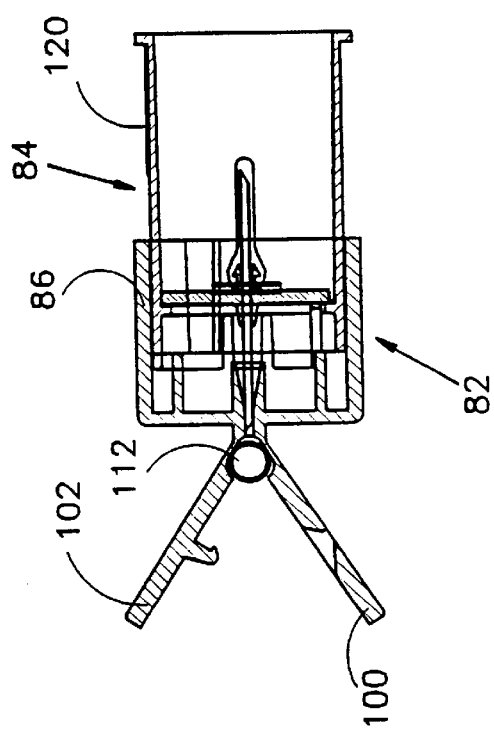
Figure 11A:
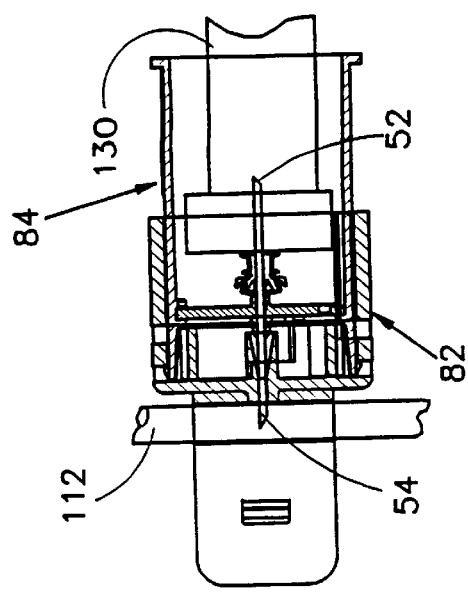
FIGS. 11A and 11B are sectional illustrations taken along respective lines 11A—11A and 11B—11B in FIG. 10.
Figure 11B:
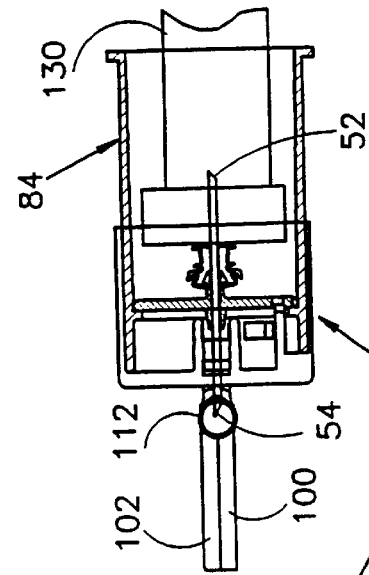

In order to use the sampling appliance 80, the user rotates the interface element 84 azimuthally to a second engagement, shown in FIGS. 7B and 9A–9B, wherein each protrusion 90 engages with apertures 94 and each relatively deep step 128 aligns with each corresponding rib 118. The needle point 54 does not yet puncture the blood conduit 112. The user then pushes the interface element 84 towards the engaging element 82, thereby disengaging each protrusion 90 from each aperture 94 and causing each protrusion 90 to engage with each corresponding aperture 96. This causes the needle point 54 to puncture the blood conduit 112. As shown in FIGS. 10–11B, the user then introduces a blood sampling tube 130 into the interface 84 so that it is punctured by the needle point 52, thereby allowing blood to be collected in the blood sampling tube 130.

Reference is now made to FIGS. 12–14B which illustrate blood sampling apparatus 140 constructed and operative in accordance with yet another preferred embodiment of the present invention. Blood sampling apparatus 140 is substantially identical with blood sampling apparatus 80 described hereinabove with reference to FIGS. 7A–14B. Like numerals label elements of blood sampling apparatus 140 which are similar to those of blood sampling apparatus 80 shown in FIGS. 7A–11B.

Figure 14A:
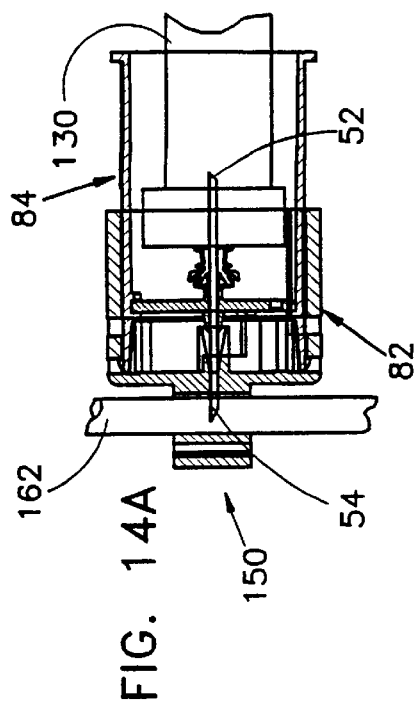
FIGS. 14A and 14B are sectional illustrations taken along respective lines 14A—14A and 14B—14B in FIG. 13.
Figure 14B:
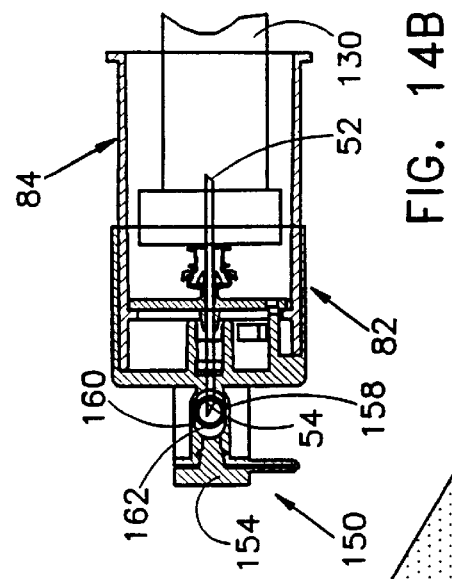
Figure 13:
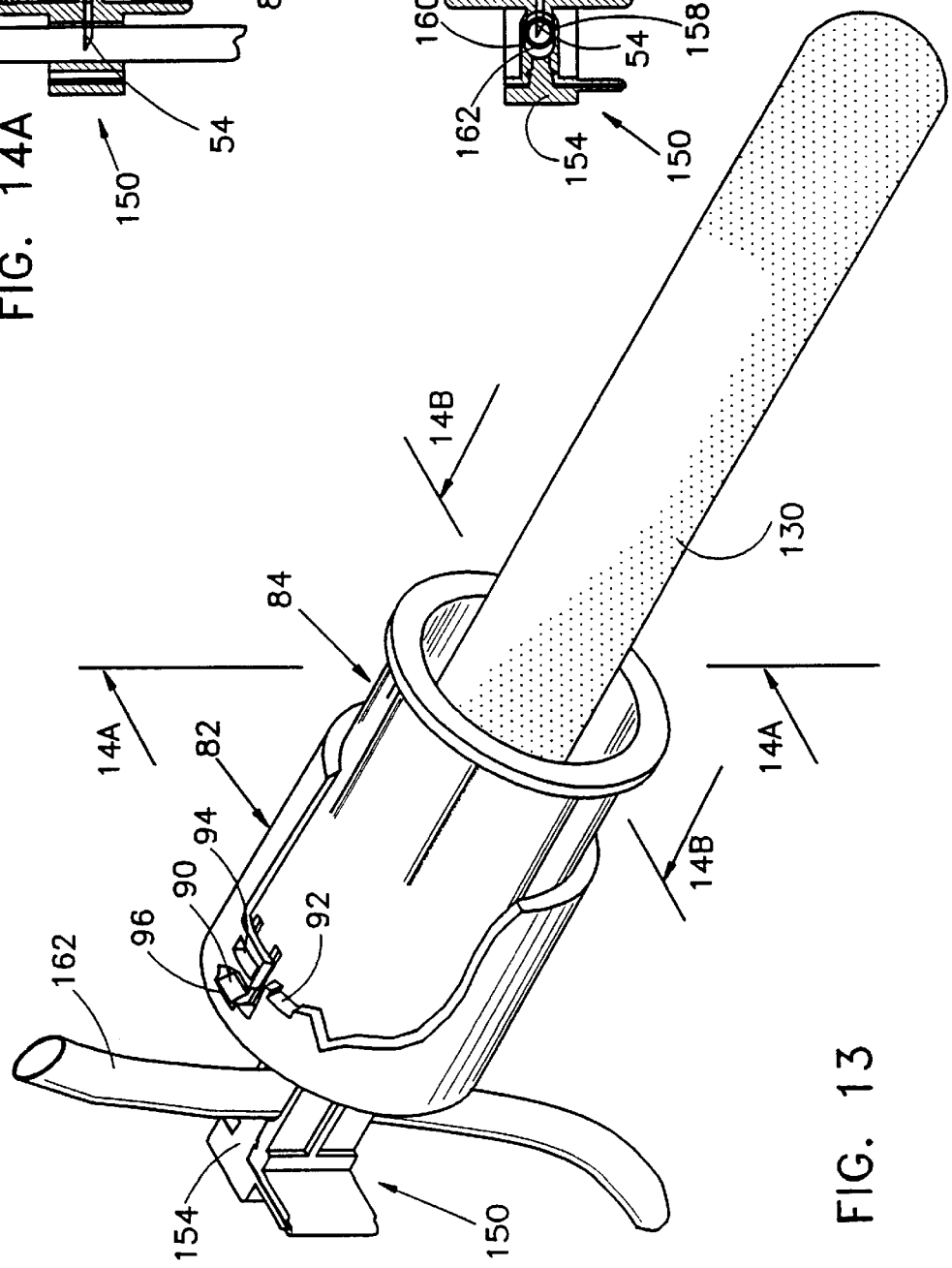
FIG. 13 is a pictorial illustration of the apparatus of FIG. 12 in operative engagement with a blood sampling tube.

Blood sampling apparatus 140 shown in FIGS. 12–14B has different hardware for clamping onto a blood conduit than blood sampling apparatus 80. Blood sampling apparatus 140 comprises a foldable clamp 150 which comprises a resilient hook 154 and a corresponding socket 156. Clamp 150 is formed with corresponding mutually facing transverse recesses 158 and 160, shown in FIG. 12, which are configured and arranged to accommodate a blood conduit 162, as shown in FIG. 13. As seen in FIGS. 13–14B, the blood conduit 162 is clamped between the recesses 158 and 160 when the hook 154 is engaged with the socket 156.

It will be appreciated by persons skilled in the art that the present invention is not limited by what has been particularly shown and described hereinabove. Rather the scope of the present invention is defined only by the claims which follow:

We claim:

1. Blood sampling apparatus comprising:
  a blood interface assembly comprising:
    an elongate housing;
    a needle mount removably mounted in said elongate housing;
    a double pointed needle fixedly mounted in said needle mount so as to have portions extending outward of said needle mount in opposite directions; and
    a puncturable resilient sheath formed over at least one portion of said needle and onto at least a portion of said needle mount;
  a blood conduit engaging element having an open-ended portion for receiving therein said blood interface assembly, and a generally closed portion opposite the open-ended portion, said generally closed portion having a passage formed therethrough, said passage being adapted for said needle to pass therethrough; and
  a clamp assembly extending from said blood conduit engaging element, said clamp assembly being operative to clamp onto an extracorporeal blood conduit, and said needle being operative, when passed through said passage, to puncture an extracorporeal blood conduit clamped by said clamp assembly, wherein said clamp assembly comprises a pair of clamp portions formed with corresponding mutually facing transverse recesses which are configured and arranged to clamp an extracorporeal blood conduit therebetween.

2. The blood sampling apparatus according to claim 1 wherein one of said clamp portions comprises a hook and the other of said clamp portions is formed with a socket, said hook being snap-engageable with said socket.

3. The blood sampling apparatus according to claim 1 wherein said blood interface assembly is engageable with said blood conduit engaging element in a first engagement orientation, wherein in said first engagement orientation said blood interface assembly cannot be moved axially out of engagement with said blood conduit engaging element, but said blood interface assembly can be rotated azimuthally about a longitudinal axis of said blood conduit engaging element to a second engagement orientation.

4. The blood sampling apparatus according to claim 3 wherein in said second engagement orientation, said blood interface assembly can be moved axially with respect to said blood conduit engaging element such that said needle can be pushed through said passage and can puncture an extracorporeal blood conduit clamped by said clamp assembly.

5. Blood sampling apparatus comprising:

an elongate housing comprising first and second generally circular cylindrical portions which are joined at a shoulder, said first portion being of larger radius than said second portion, said first portion being formed with a plurality of radially-inwardly protruding retaining tabs;

a needle mount element comprising a planar portion with a chamfered edge, said needle mount element being mounted in said elongate housing by axially pushing said needle mount element inside said first portion in a direction towards said shoulder with said chamfered edge facing said shoulder, said chamfered edge sliding past said retaining tabs such that the planar portion of said needle mount element is seated against said shoulder and retained thereagainst by said retaining tabs;

a pair of hollow, male attachment portions extending perpendicularly to said planar portion at the center of said planar portion, said planar portion and said attachment portions defining an elongate channel; and a double pointed needle extending through said elongate channel and fixedly mounted in said needle mount element so as to have needle portions extending outward of said needle mount in opposite directions.

6. The blood sampling apparatus according to claim 5 wherein said needle portions have different lengths extending perpendicularly to said planar portion outward of the needle mount in opposite directions.

7. The blood sampling apparatus according to claim 5 wherein one of said attachment portions is undercut and the other attachment portion is not undercut.

* * * * *